Dec. 1, 1964 J. GAUJARD Plant Pat. 2,456
ROSE PLANT
Filed May 6, 1963
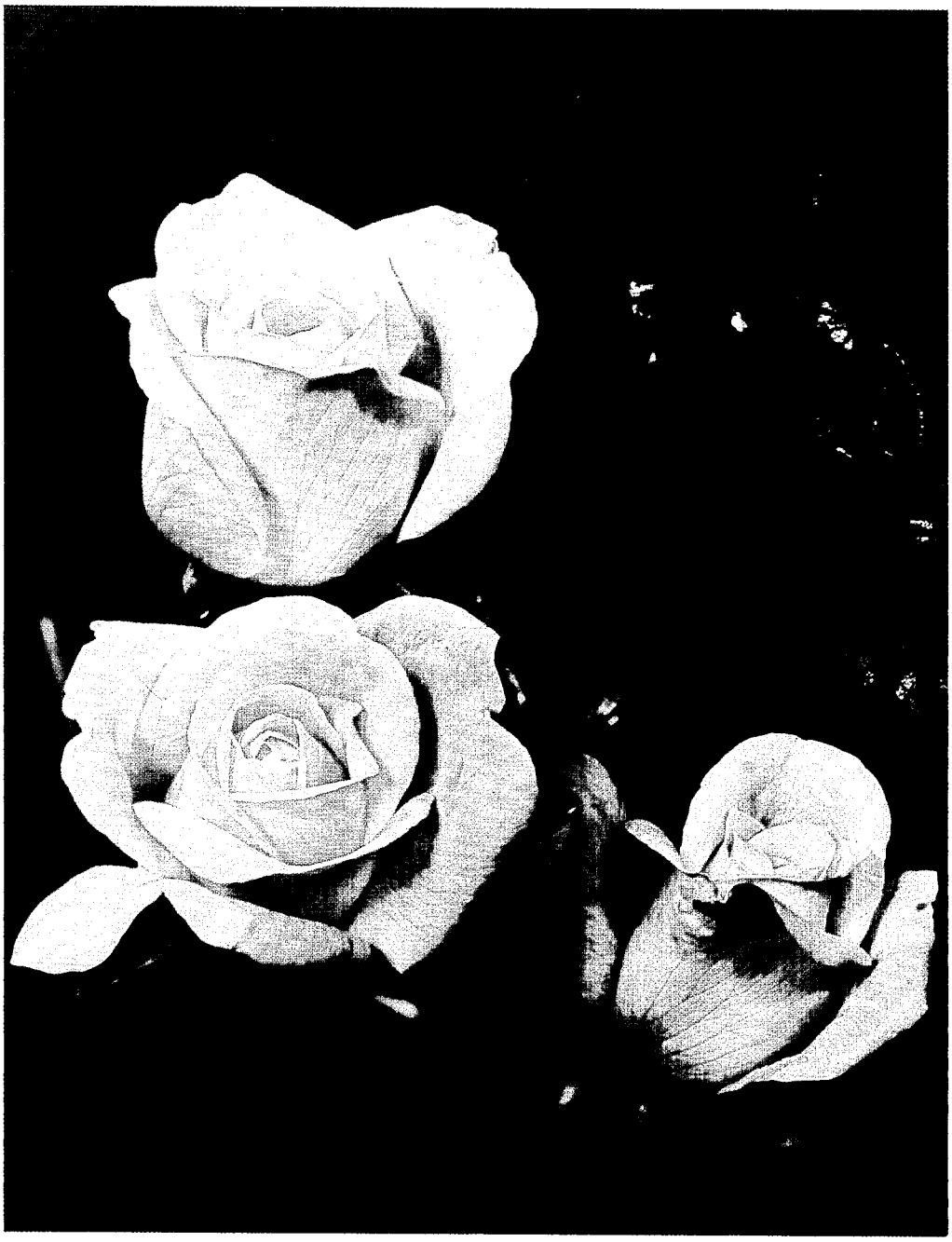
Inventor.
Jean Gaujard
By: Robert Cobb
Attorneys.

United States Patent Office

Plant Pat. 2,456
Patented Dec. 1, 1964

2,456
ROSE PLANT

Jean Gaujard, Feyzin, France, assignor to Ilgenfritz Nurseries, Inc., Monroe, Mich., a corporation of Michigan Filed May 6, 1963, Ser. No. 278,502
1 Claim. (Cl. Plt.—18)

The present invention relates to a new and distinct variety of rose plant of the hybrid tea class, which was originated by me by crossing the variety known as "Mme. Butterfly" (unpatented) with the variety known as "Fernand Arles" (unpatented).

As the result of this breeding, I have produced a new and improved rose variety which is distinguished from its parents, as well as from all other varieties of which I am aware, as evidenced by the following unique combination of characteristics which are outstanding therein:

(1) Very strong foliage which is substantially completely disease resistant, especially with respect to mildew and blackspot;

(2) A distinctive and attractive Flesh Pink general color tonality of the flowers, said color having a pearl-like sheen unlike any other rose of which I am aware; and (3) Excellent suitability for greenhouse forcing.

Asexual reproduction of the new variety by budding, as performed by me at Feyzin, France, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with the color chart entitled "Repertoire de Couleurs," prepared by Rene Oberthur, except where general color terms of ordinary dictionary significance are obvious:

Type: Hardy; greenhouse; outdoor; for cut flowers and for garden decoration.
Class: Hybrid tea.
Breeding: Seedling.
*Seed parent.*—"Mme. Butterfly."
*Pollen parent.*—"Fernand Arles."
Propagation: Holds its distinguishing characteristics through succeeding propagations by budding.

*Flower*

Locality where grown and observed: Outdoors at Feyzin, France, and in greenhouse at Antibes, France.
Flowers borne: Singly and in regular pyramidal clusters; on stems ranging from medium length to long.
Quantity of bloom: Abundant, both outdoors and in greenhouse; exceptionally abundant in greenhouse.
Continuity: Continuous.
Fragrance: Penetrating. Nature—sweetbriar.
Bud:
*Peduncle.*—Long; erect; with few green prickles. Color—grey.
*Before calyx breaks.*—Size—medium. Form—long; without foliaceous appendages on the surface of the bud; with stout foliaceous parts extending beyond the tip of the bud equal to ¼ or more of its length. Color—Flesh Pink, No. 3, page 140.
*As calyx breaks.*—Color—Flesh Pink, No. 2, page 140.
*As first petal opens.*—Size—medium. Form—pointed. Color: outside—Flesh Pink, No. 3, page 140; inside—Flesh Pink, No. 1, page 140.
*Opening.*—Opens up well.
Bloom:
*Size.*—From 3 inches to 4 inches in diameter.
*Petalage.*—Very double; from 50 to 60 petals; arranged regularly.
*Form.*—High-centered at first, and remaining high-centered; petals being at first tightly rolled outward and remaining tightly rolled outward at maturity.
Petals:
*Texture.*—Thick.
*Appearance.*—Inside—from shiny to satiny. Outside—from shiny to satiny.
*Shape.*—Outside—oval, with 3 notches. Intermediate—oval, with 3 notches. Inside—oval, with 3 notches.

This description of a newly opened flower was made from a rose grown outdoors during the month of September at Feyzin, France:

*Color.*—Outer petal: outside surface—Carolina Pink, No. 3, page 129; inside surface—Carolina Pink, No. 2, page 129. Intermediate petal: outside surface—Carolina Pink, No. 3, page 129; inside surface—Carolina Pink, No. 2, page 129. Inner petal: outside surface—Incarnat Rose, No. 4, page 134; inside surface—Incarnat Rose, No. 3, page 134.

This description of a newly opened flower was made from a rose grown in a greenhouse during the month of September at Antibes, France:

*Color.*—Outer petal: outside surface—Flesh Pink, No. 2, page 140; inside surface—Flesh Pink, No. 1, page 140. Intermediate petal: outside surface—Flesh Pink, No. 3, page 140; inside surface—Flesh Pink, No. 2, page 140. Inner petal: outside surface—Flesh Pink, No. 4, page 140; inside surface—Flesh Pink, No. 3, page 140.

This description was made from a rose that was open for three days outdoors during the month of September at Feyzin, France:

*Color.*—Outer petal: outside surface—Flesh Pink, No. 2, page 140; inside surface—Flesh Pink, No. 1, page 140. Inner petal: outside surface—Flesh Pink, No. 3, page 140; inside surface—Flesh Pink, No. 4, page 140.

This description was made from a rose that was open for three days in a greenhouse during the month of September at Antibes, France:

*Color.*—Outer petal: outside surface—Flesh Pink, No. 3, page 140; inside surface—Flesh Pink, No. 2, page 140. Inner petal: outside surface—Flesh Pink, No. 4, page 140; inside surface—Flesh Pink, No. 2, page 140.
*General color effect.*—Outdoor: newly opened flower—Flesh Pink, No. 1, page 140; 3-days open—Flesh Pink, No. 2, page 140. Greenhouse: newly opened flower—Flesh Pink, No. 2, page 140; 3-days open—Flesh Pink, No. 4, page 140.
*Behavior.*—Drop off cleanly; best in dry weather; perfect in greenhouse.
*Flower longevity.*—On bush in garden—10 days in September. Cut roses grown outdoors and kept at livingroom temperatures—10 days in September. On bush in greenhouse—6 days in September. Cut roses grown in greenhouse and kept at livingroom temperatures—10 days in September.

*Reproductive Organs*

Stamens: Few; arranged regularly; mixed with petaloids. Color—clear yellow.
Filaments: Short; without anthers. Color—yellow.
Anthers: Small. Color—white.
Pollen: Moderate abundance. Color—lemon.
Pistils: Medium number.
Styles: Very even; short; very thin; separated.
Stigma: Color—yellow.
Ovaries: All enclosed in calyx.
Hips: Pointed; globular; with conspicuous neck; rough; thick walls. Color—green.
Sepals: Recurved. Color—clear green.
Seeds: Few; small.

*Plant*

Foliage:

*Leaves.*—Compound of 5 leaflets; abundant quantity; medium size; heavy.

*Leaflets.*—Shape—oval, with apex obtuse. Base—obtuse. Margin—simply dentate.

*Color.*—Mature: upper surface—dark green; under surface—normal green. Young: upper surface—bronze red; under surface—bronze red.

*Rachis (the supporting stem of the compound leaf).*—Medium size. Upper side—smooth. Under side—extremely smooth.

*Stipules.*—Moderately short; medium width; with points turning out at an angle of less than 45°.

*Disease resistance.*—Substantially completely disease resistant, especially to mildew and blackspot, as determined by comparison with other varieties grown in France under comparable cultural conditions.

Growth:

*Habit.*—Bushy; upright; much-branched.

*Growth.*—Vigorous.

*Canes.*—Heavy.

*Main stems.* — Color — brown. Thorns — medium length; hooked upward; with long base. Prickles—few; color—brown. Hairs—few; color—brown.

*Branches.* — Color — green. Thorns — few; short; hooked upward; with short, round base. Prickles—few; color—green. Hairs—few; color—grey.

*New shoots.*—Color—brownish bronze. Thorns—few; medium length; hooked upward; with short, round base. Prickles — few; color — brown. Hairs—few; color—grey.

I claim:

A new and distinct variety of rose plant of the hybrid tea class, substantially as herein shown and described, characterized particularly as to novelty by the unique combination of very strong foliage which is substantially completely disease resistant and particularly resistant to mildew and blackspot, a distinctive and attractive Flesh Pink general color tonality of the flowers, said color having a pearl-like sheen, and excellent suitability for greenhouse forcing.

No references cited.

ABRAHAM G. STONE, *Primary Examiner.*